United States Patent [19]

Trost

[11] Patent Number: 5,743,902
[45] Date of Patent: Apr. 28, 1998

[54] HAND-HELD LASER SCANNER

[75] Inventor: David Trost, San Francisco, Calif.

[73] Assignee: Coherent, Inc., Palo Alto, Calif.

[21] Appl. No.: 377,131

[22] Filed: Jan. 23, 1995

(Under 37 CFR 1.47)

[51] Int. Cl.$^6$ ................................................. A61B 17/36
[52] U.S. Cl. ............................................... 606/18; 606/11
[58] Field of Search .................................... 606/2, 4, 5, 6, 606/10, 11, 12, 15, 16, 17

[56] References Cited

U.S. PATENT DOCUMENTS

| | | | |
|---|---|---|---|
| 4,492,230 | 1/1985 | Sunago et al. | 128/303.1 |
| 4,887,019 | 12/1989 | Reis et al. | 606/4 |
| 5,125,923 | 6/1992 | Tanner et al. | 606/10 |
| 5,219,347 | 6/1993 | Negus et al. | 606/19 |
| 5,360,447 | 11/1994 | Koop | 623/15 |
| 5,364,390 | 11/1994 | Taboada et al. | 606/4 |
| 5,411,502 | 5/1995 | Zair | 606/10 |
| 5,480,396 | 1/1996 | Simon et al. | 606/4 |
| 5,533,997 | 7/1996 | Ruiz | 606/5 |

FOREIGN PATENT DOCUMENTS

| | | |
|---|---|---|
| 0 326 760 | 8/1989 | European Pat. Off. .... A61B 17/36 |
| 0 714 642 A1 | 6/1996 | European Pat. Off. . |
| 0 724 866 A1 | 8/1996 | European Pat. Off. . |
| WO 93/03521 | 2/1993 | WIPO .................... H01S 3/08 |

OTHER PUBLICATIONS

Sharplan SipkTouch™ Scanner User's Manual Prepared Oct. 1994—pp. 1–8.
Sharplan Swiftlase™ Flashscan Leaflet Cat. No. PB2344100 Prepared Jun. 1993—pp. 1–6.
Sharplan 771B Laser Microscan User's Manual Prepared Jul. 1985 Laser Industries Ltd.—pp. 1–29.
Copy of International Search Report, issued Jul. 5, 1996, in PCT/US96/01080, 5 pages in length.

*Primary Examiner*—Lee S. Cohen
*Assistant Examiner*—Sonya Harris-Ogugua
*Attorney, Agent, or Firm*—Limbach & Limbach L.L.P.

[57] ABSTRACT

A surgical laser scanner having optics that scans a pulsed laser beam onto a target tissue is disclosed. The laser scanner has a lens and a scanning mirror or mirrors located upstream of the lens at a distance substantially equal to the focal length of the lens. The laser beam hits the scanning mirror and is reflected onto the lens in a pattern defined by sequential positions of the scanning mirror. The laser beam is projected onto the target tissue by the lens in a direction parallel to the optical axis of the lens. The projected pattern has a constant size regardless of the distance between the laser scanner and the target tissue.

18 Claims, 7 Drawing Sheets

HAND-HELD LASER SCANNER

BACKGROUND OF THE INVENTION

1. Field of the Invention

This invention relates generally to medical lasers, and relates more particularly to a hand-held laser scanner that generates a scanned pattern of constant size regardless of the positioning of the laser scanner with respect to a treatment surface.

2. Description of the Relevant Art

Historically, surgical incisions in tissue have been performed with sharp metal cutting instruments. More recently, lasers have become the tool of choice in many medical procedures to cut and treat tissue. Laser beams can be accurately focused on tissue to cut many desired shapes and depths. The slit incision, a very narrow elongated incision, is especially appropriate for laser surgery. Surgeons can make these narrow incisions by passing a focused laser beam over the target tissue.

One medical procedure where slit incisions are desired is hair transplants. Hair transplants have become a common cosmetic procedure, particularly for the treatment of male pattern baldness. In a hair transplant procedure, a piece of the patient's skin having healthy growing hair is removed from a donor region on the scalp and implanted into a hairless, recipient region. This process involves cutting a hole or slit into the recipient region so that the new plug of hair can be inserted. Slit grafting is modernly used because of its many cosmetic and medical advantages over circular punching.

Historically, slit grafting has been accomplished by cutting a slit into the recipient region with a scalpel. More recently, lasers have been used. A laser is more advantageous because the size and shape of the incision can be more accurately controlled. A laser beam, usually a pulsed infrared beam, is focused onto the scalp. The exposure can be controlled to remove the amount of skin needed for the hair graft dimensions. Another advantage of using lasers to cut or remove skin is the coagulating effects of the laser light that minimizes bleeding and pain. Further, the laser radiation removes the skin in the slit it creates thereby creating room for the new plug of hair to be placed inside. A laser assisted hair transplant method is described in U.S. Pat. No. 5,360,447, which is assigned to Coherent, Inc, the assignee of the present application.

A laser beam can be accurately focused on the scalp by a variety of optical delivery systems. One such system is marketed by Coherent, Inc. in conjunction with its sealed carbon dioxide medical laser system under the name Ultrapulse 5000. To create a slit, the surgeon positions the output of the optical delivery system so that the beam will impinge on the target tissue. The surgeon then presses a footswitch which opens a shutter that allows light to exit the output end of the optical delivery system. The doctor then moves the output end over the target tissue until the desired slit width and depth is created. This procedure is followed for every slit made in the target tissue.

The drawback to this optical delivery system is that it takes time and skill to create a series of slits of the desired dimensions and layout. Since the number of slits required can be as numerous as the number of individual hair follicles being transplanted, the time and skill required to create accurate slits in the recipient area can be great. Furthermore, the placement of each slit is important, because uniform patterns give a more natural appearance of the transplanted hair. Thus, there is a need for an optical delivery system that creates multiple slits in uniform patterns.

Lasers are also used surgically to treat relatively large areas of tissue in techniques such as ablation to remove disfigured skin. The spot diameter of the laser beam is typically larger in size and lower in power density as compared to lasers used to make incisions. Even though the spot diameter of the laser beam is relatively large, the area of treatment is usually larger than the area of the spot, which requires that the beam be scanned or otherwise moved across the area to be treated.

One approach to moving the laser beam across a treatment area is to scan the beam like a raster, back and forth in successive rows until the area is covered. One drawback to that approach is that successive rows can overlap with insufficient recovery time in between scans of successive rows, which can damage the tissue in the areas of overlap. Another drawback is that the pattern area covered by the laser can be dependent on the distance between the treatment area and the scanning device, which is not easily controlled if the laser instrument is handheld by the surgeon.

There is thus a need for an optical delivery system that creates an scanned laser beam in a uniform pattern regardless of the precise position of the treatment surface with respect to the laser instrument.

SUMMARY OF THE INVENTION

In accordance with the illustrated preferred embodiments, the present invention is a surgical laser handpiece that scans a laser beam onto a target tissue. The surgical handpiece, or hand-held laser scanner, has a lens and a scanning mirror located at a distance from the lens that is equal to or substantially equal to the focal length of the lens. The laser beam hits the scanning mirror and is reflected onto the lens in a pattern defined by multiple positions of the scanning mirror. The lens projects the laser beam pattern onto the target tissue so that the output beam exits the lens parallel to the optical axis of the lens. The projected pattern has a constant size regardless of the distance between the handpiece and the target tissue. In other words, any variation in the size of the pattern projected onto the target tissue is minimal as the spacing between the lens and the target tissue is varied.

In another aspect of the present invention, the laser beam incident on the scanning mirror can be focused light or collimated light. If the laser beam is focused on the scanning mirror, then the lens collimates the beam, resulting in an output beam having a spot size that does not vary with changing distance between the handpiece and the target tissue. The spot size of this output beam can be adjusted by varying the cone angle of the incident focused beam. If the laser beam incident on the scanning mirror is collimated, then the lens focuses the output beam, thus providing a concentrated laser beam useful for incisions. Beam conditioning optics located upstream of the scanning mirror can be used to focus the laser beam on the scanning mirror, to adjust the cone angle of the focused beam, and to adjust the size of the collimated laser beam incident to the scanning mirror. Preferably, the surgical handpiece of the present invention has two mirrors that are independently rotatable about orthogonal axes. The two independently rotatable mirrors permit two-dimensional patterns of the output beam to be generated.

Another aspect of the present invention is a method of scanning a laser beam onto a target tissue by generating a laser beam and delivering it to a scanning mirror, pivoting the scanning mirror to project the laser beam onto a lens, where the scanning mirror is one focal length upstream of the lens, and projecting the laser beam through the lens and onto the target tissue.

Still another aspect of the present invention is a method of ablating tissue using a laser beam by positioning an output end of a delivery device adjacent the tissue, energizing the laser to generate a laser beam, directing the laser beam within the delivery device through a scanning mirror and then a lens to the tissue, where the scanning mirror is located approximately one focal length from the lens so that the lens projects the laser beam along a path parallel to an optical axis of the lens, and moving the scanning mirror to project a pattern of laser beams on the tissue to be ablated.

The features and advantages described in the specification are not all inclusive, and particularly, many additional features and advantages will be apparent to one of ordinary skill in the art in view of the drawings, specification and claims hereof. Moreover, it should be noted that the language used in the specification has been principally selected for readability and instructional purposes, and may not have been selected to delineate or circumscribe the inventive subject matter, resort to the claims being necessary to determine such inventive subject matter.

BRIEF DESCRIPTION OF THE DRAWINGS

FIG. 11 is a diagram of several scanning patterns utilized with the hand-held laser scanner of FIG. 1.

FIG. 12 is a diagram of several scanning patterns utilized with the hand-held laser scanner of FIG. 2.

DETAILED DESCRIPTION OF THE PREFERRED EMBODIMENT

FIGS. 1 through 12 of the drawings depict various preferred embodiments of the present invention for purposes of illustration only. One skilled in the art will readily recognize from the following discussion that alternative embodiments of the structures and methods illustrated herein may be employed without departing from the principles of the invention described herein.

Figure 1:
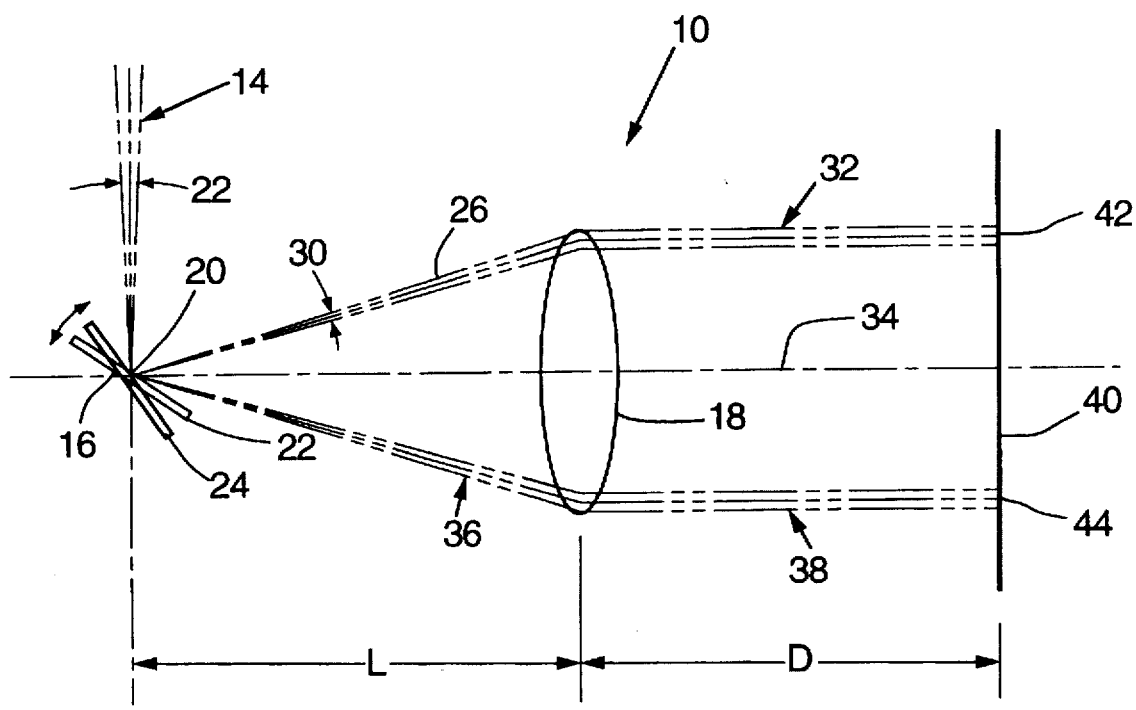
FIG. 1 is a schematic view of a scanning mirror that receives a focused laser beam and a lens that projects a pattern of collimated laser beams, which is used in one embodiment of a hand-held laser scanner according to the present invention.

The preferred embodiment of the present invention is a hand-held laser scanner or surgical handpiece that scans a laser beam in a uniform pattern over a target tissue. The theory of operation of the laser scanner 10, 12 can be explained by reference to FIGS. 1 and 2. In FIG. 1, an incident laser beam 14 is focused on a scanning mirror 16, which reflects the laser beam onto a lens 18. The scanning mirror 16 pivots so that the laser beam strikes the mirror at a point 20 that is one focal length L upstream of and along the optical axis of the lens.

The scanning mirror 16 moves between position 22 and position 24. At position 22, the mirror 16 reflects the laser beam to the top of the lens 18 along path 26. The angle 28 of the incident beam is the same as the angle 30 of the reflected beam along path 26 because the mirror 16 is a flat mirror. Each ray of the reflected beam is refracted by the lens 18 to a path 32 that is parallel to an optical axis 34 of the lens. The result is that the output laser beam is collimated and parallel to the optical axis 34.

When the scanning mirror 16 is at position 24, the incident laser beam 14 is reflected by the mirror to the bottom of the lens 18 along path 36. The lens refracts the laser beam to an output path 38 that is also parallel to the optical axis 34. The output laser beam is collimated because the beam incident on the lens 18 originates from the point 20, which is one focal length L from the lens.

The target tissue 40 is located at the output side of the lens 18. The two output beams 32 and 38 form a simple pattern of two spots 42, 44 on the target tissue. The position of the laser beam spots 42, 44 projected onto the target tissue 40 is a function of the mirror angle only. Positioning the scanning mirror 16 between position 22 and position 24 will result in spots in the pattern between spots 42 and 44. Note that the distance between the two spots 42, 44 does not vary with the separation distance D between the lens 18 and tissue 40. In other words, the size of the pattern of the projected laser beam spots is constant, regardless of the position of the target tissue relative to the laser scanner. Also, the size of the laser beam spots 42, 44 is constant regardless of the separation distance between the lens 18 and tissue 40 because the output beams are collimated.

The laser scanner 10 is hand-held by the operator, which makes it difficult to maintain a constant distance between the laser scanner and the target tissue without adding cumbersome jigs or support structures. The present invention eliminates concern over the separation distance D between the scanner and the target tissue because both the pattern area and the spot size are not affected by changes in the separation distance.

Figure 2:
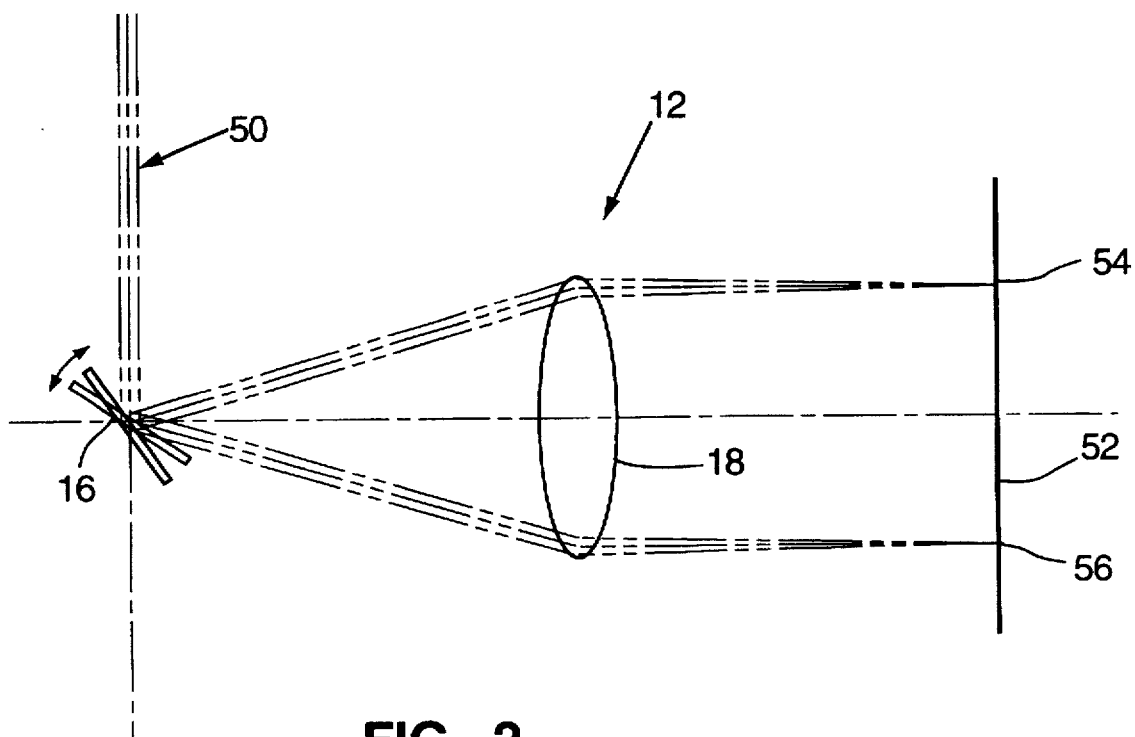
FIG. 2 is a schematic view of a scanning mirror that receives a collimated laser beam and a lens that projects a pattern of focused laser beams, which is used in another embodiment of a hand-held laser scanner according to the present invention.

An alternative preferred embodiment of the present invention, the laser scanner 12 shown in FIG. 2, is very similar to the laser scanner 10 of FIG. 1, with the exception of the incident and output laser beams. In this case, the incident laser beam 50 is collimated instead of focused. Collimated beams are reflected along paths 26 and 36, or some intermediate path, depending on the angle or position of the scanning mirror 16. The lens 18 refracts the collimated beams so that they focus at a focal plane 52 on the output side of the lens 18. The spots 54 and 56 of the pattern thus projected onto the target tissue are focused, small diameter spots. Again, the relative positioning of the spots within the pattern does not change as a function of the separation distance between the lens 18 and the target tissue. The spot size does change somewhat as a function of the separation distance between the target tissue and the focal plane 52, but the variation is not great, which allows for some movement of the laser scanner relative to the target tissue.

FIGS. 1 and 2 show how the invention works in one dimension. In the preferred embodiments, the laser scanner of the present invention produces a two-dimensional pattern by using a mirror or system of mirrors that project the laser beam onto the lens 18 in a two-dimensional pattern.

Figure 3:
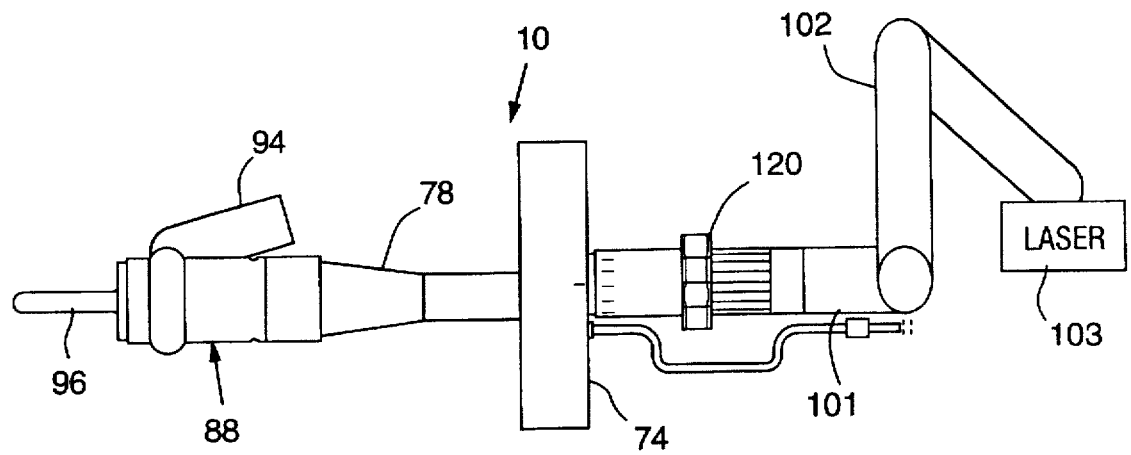
FIG. 3 is an overall view of a hand-held laser scanner according to the present invention.
Figure 4:
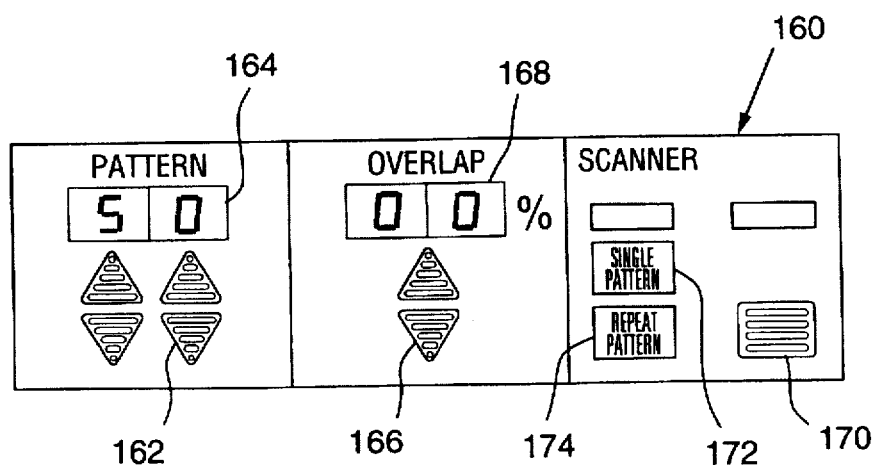
FIG. 4 is a diagram of a control panel for the hand-held laser scanner.
Figure 5:
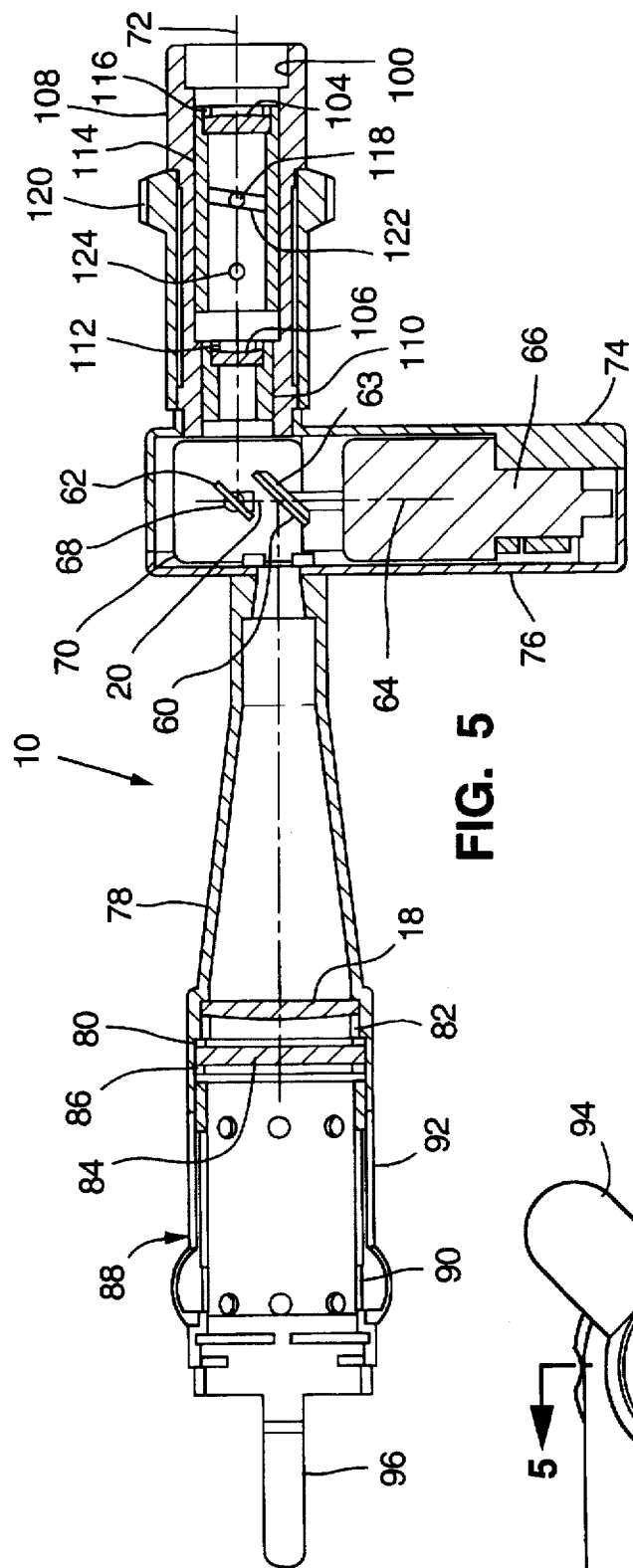
FIG. 5 is a sectional view of the hand-held laser scanner of FIG. 1.
Figure 6:
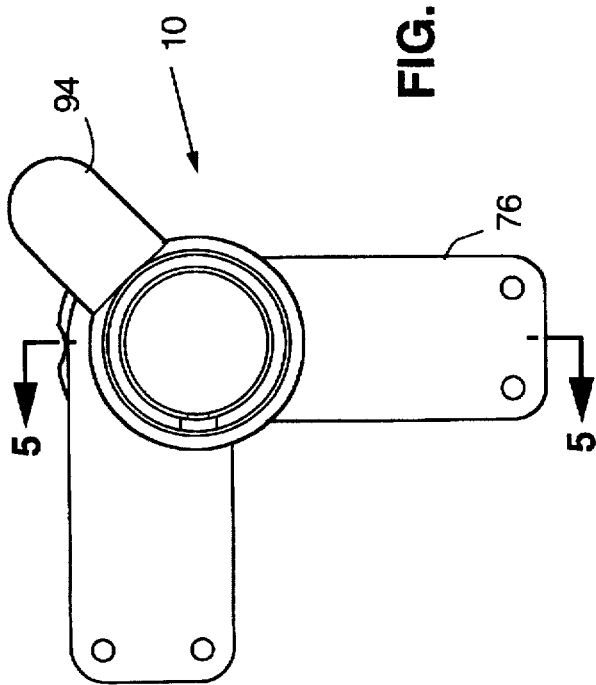
FIG. 6 is an end view of the hand-held laser scanner of FIG. 1.
Figure 7:
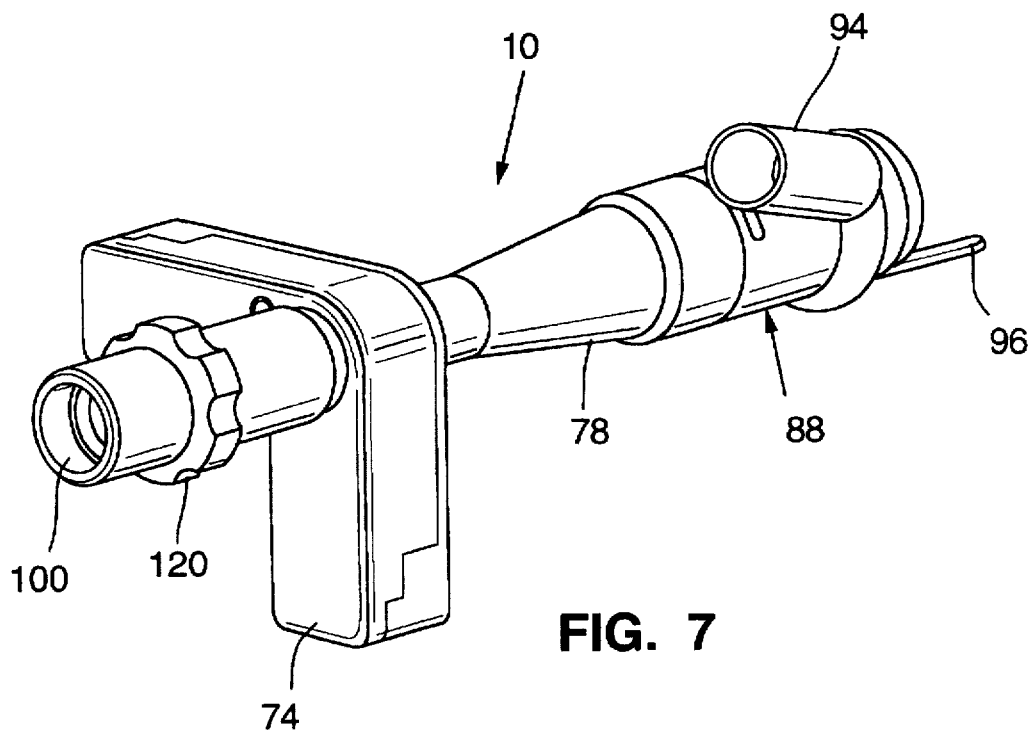
FIG. 7 is a perspective view of the hand-held laser scanner of FIG. 1.

The laser scanner 10 is further illustrated in FIGS. 3–7. As shown in FIG. 5, the laser scanner 10 has two independently controlled mirrors 60, 62 that scans the laser beam in two orthogonal directions. Mirror 60 is mounted on a mirror mount 63 and is pivoted about axis 64 by a rotary galvanometer 66. Mirror 62 is pivoted about an axis 68 by another rotary galvanometer 70. The axes of rotation of the mirrors 60, 62 are mutually orthogonal and are also orthogonal to the incident laser beam 72. The galvanometers 66, 70 are powered and controlled by a controller (not shown) that supplies appropriate voltages to the galvanometers to cause them and the attached mirrors to rotate to the desired positions. The two mirrors 60, 62 are separated by a small clearance to allow the two mirrors to move independently. The point 20, which is one focal length away from the lens 18, is located between the two mirrors, which causes a small deviation from the ideal situation where the mirrors would be coincident with point 20.

The laser scanner 10 also includes a frame 74 and a cover 76 that houses the galvanometers 66 and 70. An exit tube 78 is attached to the frame 74 and provides a mounting for lens 18, a lens retainer 80, a spacer 82, a window 84, and a window retainer 86. At a distal end of the exit tube 78 is a smoke evacuation tip 88, including an inner tube 90, an outer sleeve 92, and a port 94. Also at the distal end of the assembly is a spatula 96.

As shown in FIGS. 3 and 5, the laser input end of the laser scanner 10 has an internally-threaded coupling 100 that attaches the laser scanner to the distal end 101 of an articulated arm 102 of a laser 103. (FIG. 3 is not to scale). In the preferred embodiment, the laser beam is created by the Ultrapulse 5000, a carbon dioxide laser manufactured and sold by Coherent, Inc. The Ultrapulse 5000 produces a pulsed infrared laser beam having maximum specifications of 500 mj per pulse, a pulse duration of up to 1 ms, at a repetition rate of 500 Hz, for an average power of 250 Watts.

As shown in FIG. 5, between the coupling 100 and the mirrors 60, 62 are beam conditioning optics that focus the collimated input laser beam to the point 20, which is one focal length of lens 18 away from the lens. The beam conditioning optics includes two lenses 104, 106 mounted in a telescope body 108. Lens 106 is fixed and is mounted in a lens holder 110 and retained by a retainer 112. Lens 104 is movable and is mounted in a lens holder 114 by a retainer 116. The lens holder 114 is rotatably mounted within the telescope body 108. A drive pin 118 is mounted to the inside of an adjustment knob 120 and engages a helical slot 122 in the outside of the lens holder 114. The position of the lens 104 is adjusted by rotating the adjustment knob 120. A guide pin 124 attached to the lens holder 114 rides in an axial slot in the telescope body 108 and prevents the lens holder 114 from rotating. As shown in FIG. 3, the adjustment knob 120 is calibrated to indicate the approximate diameter of the spot of the output beam.

The design of the optics necessary to produce the desired beam dimensions will vary depending on the configuration of optical elements used and the characteristics of the laser beam as it enters the handpiece. In the preferred embodiment of laser scanner 10, lens 104 has a focal length of +50 mm, lens 106 has a focal length of −10 mm, and lens 18 has a focal length of +100 mm. The beam diameter of the laser beam supplied by laser 103 is about 6 mm. The output beam diameter is adjustable over the range of about 2 mm to 4 mm. The lens are preferably made from zinc selenide and the mirrors are preferably made from molybdenum. The lens 104 and 106 focus the laser beam to a spot diameter of about 0.5 mm at the scanning mirrors.

Figure 10:
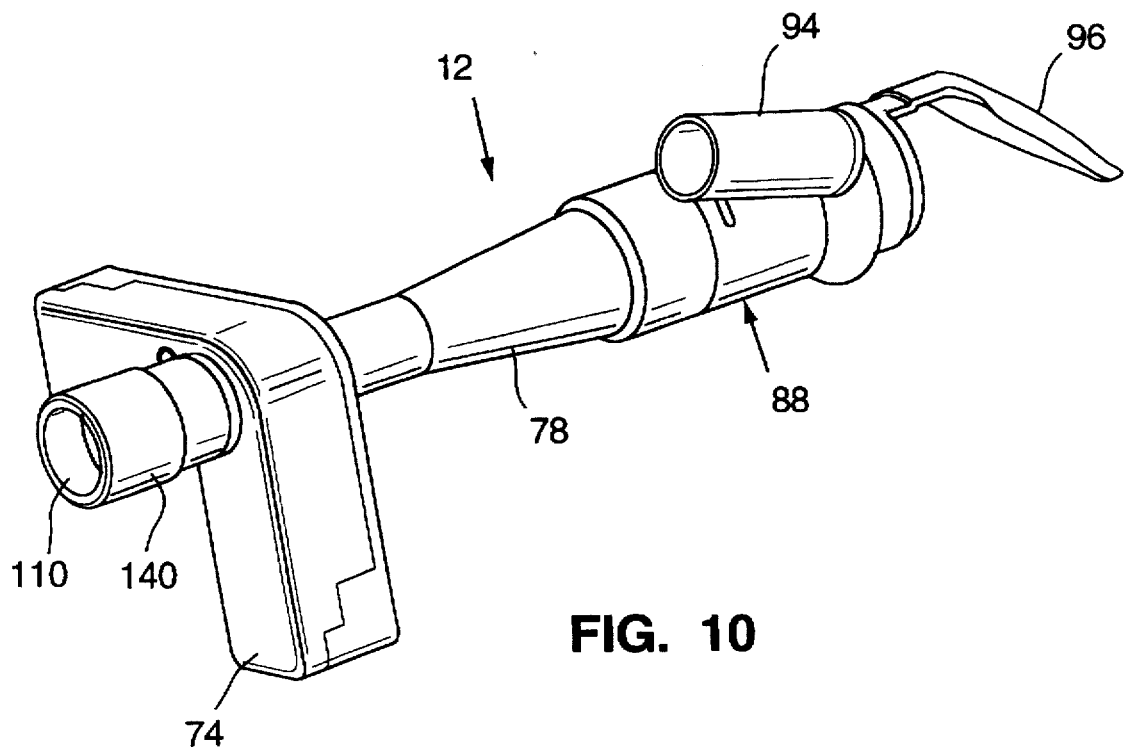
FIG. 10 is a perspective view of the hand-held laser scanner of FIG. 2.
Figure 8:
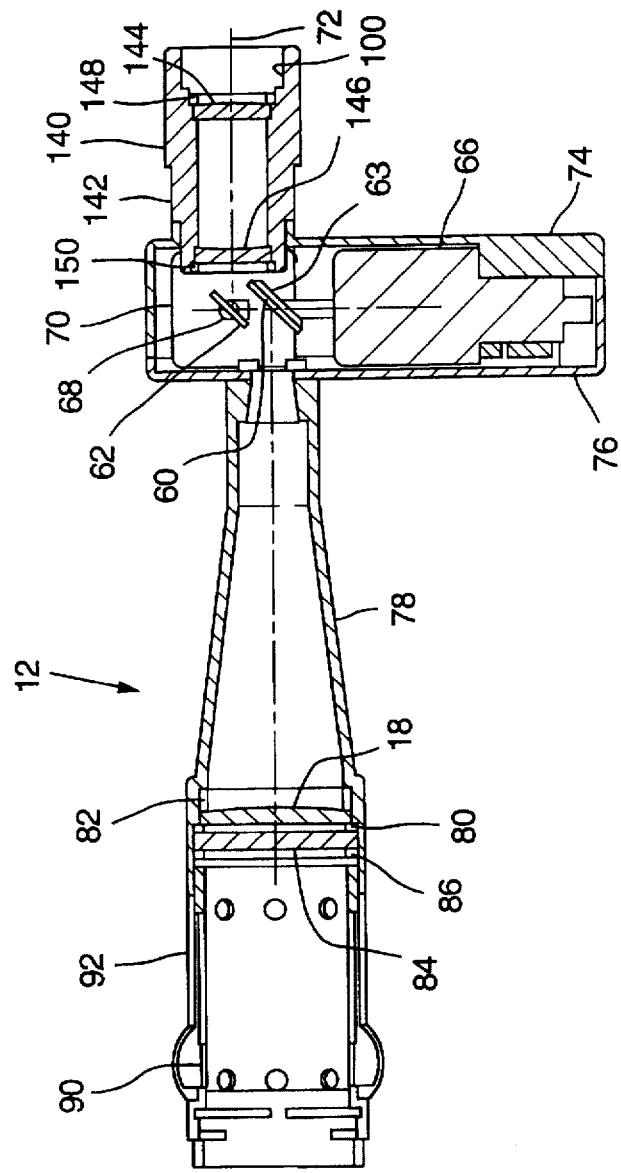
FIG. 8 is a sectional view of the hand-held laser scanner of FIG. 2.
Figure 9:
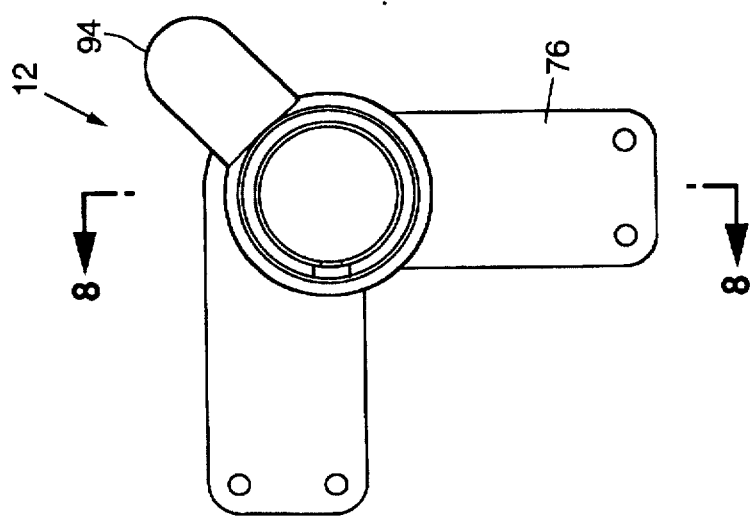
FIG. 9 is an end view of the hand-held laser scanner of FIG. 2.

The construction of the other preferred embodiment of the present invention, laser scanner 12, is shown in FIGS. 8–10. Laser scanner 12 is similar in construction to laser scanner 10 (FIGS. 5–7) except for the beam conditioning optics 140. As shown in FIG. 8, the beam conditioning optics 140 of laser scanner 12 has a body 142 that is mounted to the frame 74. Lens 144 and 146 are retained in the body 142 by retainers 148 and 150, respectively. The lenses 144, 146 reduce the diameter of the incoming laser beam 72 to a smaller diameter and supplies a collimated laser beam to the mirrors 60, 62. The incoming laser beam 72 is collimated, so if its diameter is acceptable, then the lenses 144, 146 can be eliminated.

In the preferred embodiment of laser scanner 12, lens 144 has a focal length of +50 mm, lens 146 has a focal length of −25 mm, and lens 18 has a focal length of +100 mm. The lenses 144 and 146 change the spot diameter of the incident laser beam from about 6 mm to about 3 mm at the point where the beam strikes the mirrors. The spot diameter of the output beam is about 0.5 mm at the focal plane 52.

Figure 11:
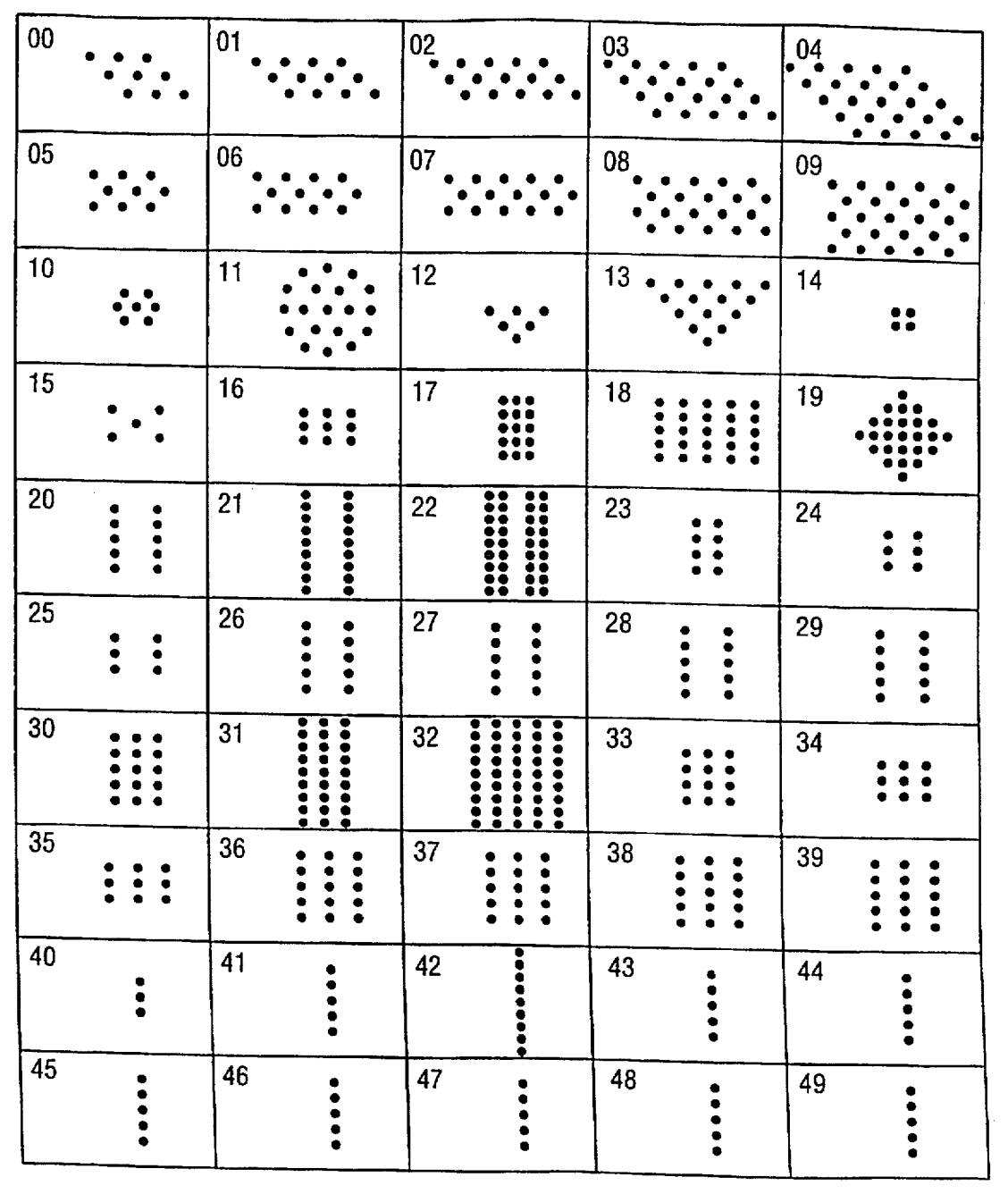
Figure 12:
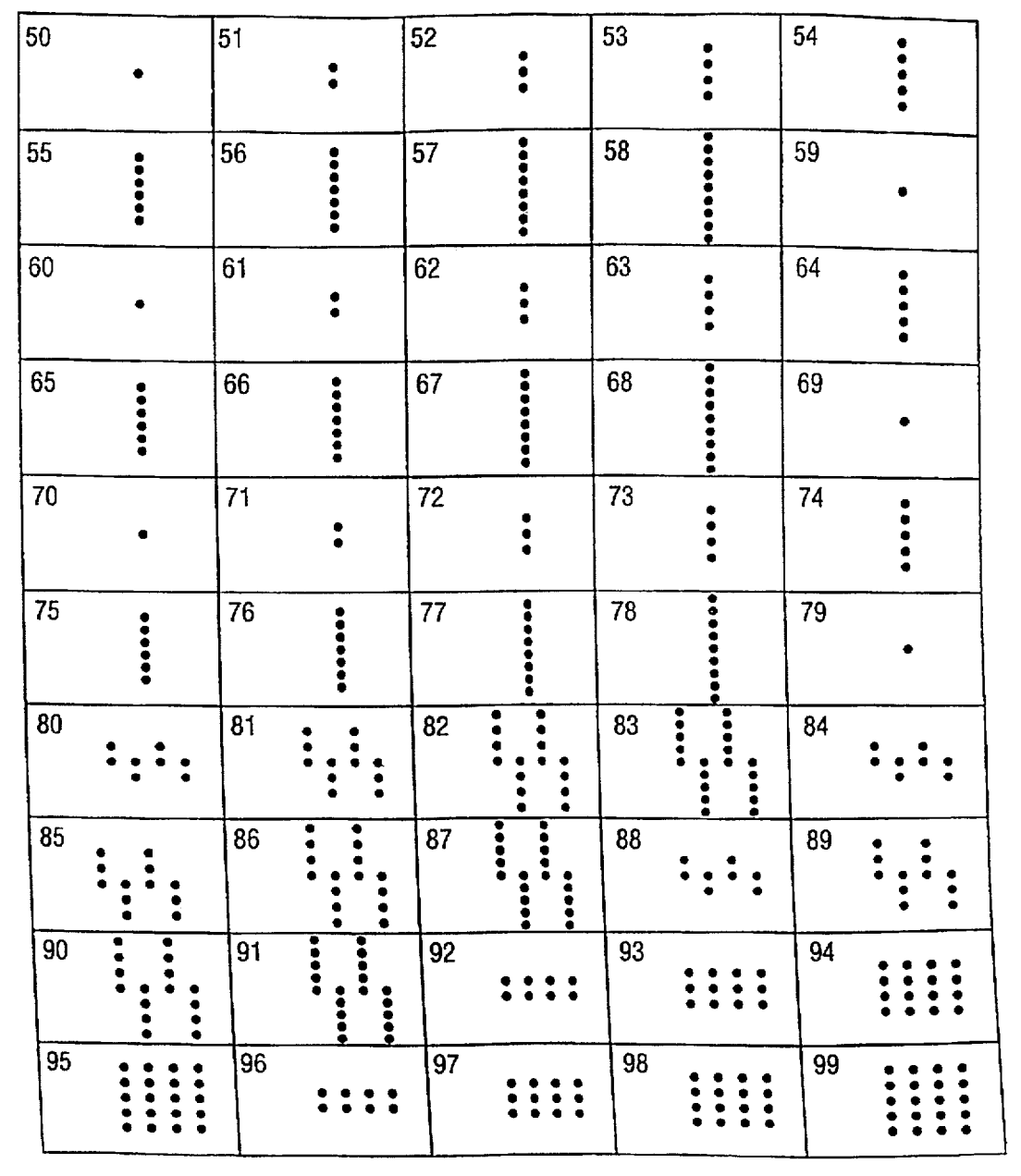

FIG. 4 illustrates a control panel 160 used with the laser scanner 10, 12. The operator selects a numbered pattern by entering two digits with a key pad 162. The pattern number is displayed by a display 164. FIGS. 11 and 12 show various patterns that can be utilized with the laser scanner 10 or 12, respectively. The operator also selects a percentage overlap by a key pad 166. The overlap value is displayed by display 168. A controller (not shown) uses the overlap value to adjust the relative spacing of the spots in the selected pattern to yield the desired overlap. The operator can also select on the control panel 160 using button 170 whether the pattern is to be delivered once or repeatedly, as indicator by indicators 172, 174.

In operation, the operator selects a pattern, an overlap, and single/repeat scanning on the control panel 160 of the laser scanner. The operator also turns on the laser system and opens a manual safety shutter. A low-power visible beam supplied by the laser is used to aim the laser scanner on the target tissue. The operator then depresses a footswitch that causes the scanner to produce a complete treatment pattern by positioning the mirrors synchronously with the pulse rate of the laser beam. In other words, the mirrors are positioned for delivery of one spot when the first laser pulse arrives; then the mirrors are repositioned for delivery of the next spot when the next laser pulse arrives; and so on until the entire pattern is completed. If a single pattern is selected, the laser scanner stops after completing the pattern, even if the footswitch is still depressed. If a repeat pattern is selected, the treatment pattern will be repeated with a one-second delay between patterns until the footswitch is released. Early release of the footswitch in either single pattern or repeat pattern mode will terminate the treatment beam before the pattern is completed.

The above-described preferred embodiments utilize an axisymetric lens 18 and two mirrors 60, 62 that are located close to the point 20, which is one focal length upstream from the lens 18. This arrangement has a small error because the laser beam does not strike both mirrors at point 20. Alternatively, a single mirror could be used along with a mechanism that would permit rotation in two dimensions about the point 20. Also alternatively, the lens could be ground anamorphic, having two different focal lengths in two orthogonal planes. This would permit each of the two mirrors to be placed one focal length upstream from the lens without interfering with their independent movement. Such an anamorphic lens could have either a toroidal surface, or two opposed cylindrical surfaces located orthogonally on opposite sides of the lens.

Another alternative for the optics design would be to have a series of a first mirror, a first lens, a second mirror and a second lens. The first lens produces an image of the first mirror on top of the second mirror, and the second mirror is one focal length upstream from the second lens. The two mirrors appear to be in the same place, approximately one focal length from the second lens. Each mirror provides pattern deflection in one of two mutually orthogonal directions.

From the above description, it will be apparent that the invention disclosed herein provides a novel and advantageous surgical laser handpiece that scans a laser beam onto a target tissue. The foregoing discussion discloses and describes merely exemplary methods and embodiments of the present invention. As will be understood by those familiar with the art, the invention may be embodied in other specific forms without departing from the spirit or essential characteristics thereof. Accordingly, the disclosure of the present invention is intended to be illustrative, but not limiting, of the scope of the invention, which is set forth in the following claims.

What is claimed is:

1. A surgical handpiece for connection to a laser that generates a laser beam, wherein the handpiece scans the laser beam onto a target tissue, the handpiece comprising:

a housing having an input end and an output end;

a scanning mirror means mounted in the housing for reflecting a laser beam entering the housing input end; and a lens mounted in the housing onto which the scanning mirror means reflects the laser beam and through which the laser beam is refracted through the housing output end and onto the target tissue, wherein the lens has a focal length and the scanning mirror means is located at a distance from the lens that is substantially equal to the focal length so that any variation in the size of a pattern projected onto the target tissue is minimal as the spacing between the housing and the target tissue is varied.

2. A surgical handpiece as recited in claim 1 wherein the scanning mirror means comprises two mirrors independently rotatable about two axes that are orthogonal to each other and orthogonal to the laser beam.

3. A surgical handpiece as recited in claim 2 wherein the scanning mirror means further comprises two galvanometers, wherein each galvanometer is coupled to a mirror by a means that permits rotation of the mirror about an axis.

4. A surgical handpiece as recited in claim 2 wherein said lens is anamorphic and has two focal lengths in two orthogonal planes, and wherein the two scanning mirrors are located at distances from the lens substantially equal to said two focal lengths.

5. A surgical handpiece as recited in claim 2 wherein said lens includes two separate lenses, wherein said lenses and mirrors are arranged along an optical path of the laser beam that includes a first rotatable mirror, then a first lens, then a second rotatable mirror, and then a second lens, wherein the first lens produces an image of the first mirror at the second mirror, and wherein the second mirror is located at a distance from the second lens substantially equal to the focal length of the second lens.

6. A surgical handpiece as recited in claim 1 further comprising beam conditioning optics located between the laser and the scanning mirror means and including optical means for providing a focused beam to the scanning mirror means.

7. A surgical handpiece as recited in claim 1 further comprising beam conditioning optics located between the laser and the scanning mirror means and including optical means for providing a focused beam having an adjustable cone angle to the scanning mirror means.

8. A surgical handpiece as recited in claim 1 further comprising beam conditioning optics located between the laser and the scanning mirror means and including optical means for providing a collimated beam to the scanning mirror means.

9. A surgical handpiece that receives a laser beam and produces a pattern of laser spots on a target tissue, the handpiece comprising:

a housing having an input end and an output end;

means mounted in the housing for scanning a laser beam entering the housing input end in a pattern; and optical means mounted in the housing for projecting the laser beam through the housing output end and onto the target tissue in a pattern of laser spots having locations that are independent of spacing between the housing and the target tissue.

10. A surgical handpiece for connection to a laser that generates a laser beam, wherein the handpiece scans the laser beam in a two-dimensional pattern onto a target tissue, the handpiece comprising:

a housing having an input end and an output end;

beam conditioning optics located at the input end of the housing;

two mirrors rotatably mounted in the housing that are independently rotatable about two axes that are orthogonal to each other and orthogonal to the laser beam, wherein the mirrors are positioned adjacent each other within the handpiece housing such that a laser beam exiting the beam conditioning optics strikes the mirrors;

means for independently rotating the mirrors; and a lens mounted in the housing onto which the mirrors reflect the laser beam and through which the laser beam is refracted through the housing output end and onto the target tissue, wherein the lens has a focal length and the mirrors are located at a distance from the lens that is substantially equal to the focal length so that any variation in the size of a pattern projected onto the target tissue is minimized as the spacing between the housing and the target tissue is varied.

11. A surgical system for scanning a laser beam onto a target tissue comprising:

means for generating a laser beam;

a handpiece housing connected to the generating means with an input end for receiving the laser beam;

means located in the handpiece housing for scanning the laser beam through an output end of the housing and across the target tissue, said means for a scanning having a scanning mirror means mounted in the housing for reflecting the laser beam, and having optical means mounted in the housing for projecting the laser beam through the handpiece output end and onto the target tissue in a pattern parallel to an optical axis of the optical means, wherein the optical means has a focal length and the scanning mirror means is located at a distance from the optical means that is substantially equal to the focal length.

12. A surgical system as recited in claim 11 wherein the means for scanning the laser beam further includes optical means for focusing the laser beam proximate the scanning mirror means.

13. A surgical system as recited in claim 11 wherein the means for scanning the laser beam further includes optical means for providing a collimated laser beam to the scanning mirror means.

14. A method of scanning a laser beam onto a target tissue, said method comprising the steps of:

generating a laser beam and delivering the laser beam to a scanning mirror rotatably mounted in a handpiece housing; moving the scanning mirror to project the laser beam onto a lens mounted in the handpiece housing, wherein the lens has a focal length and the scanning mirror is located at a distance from the lens substantially equal to the focal length; and projecting the laser beam through the lens, through an output end of the handpiece housing, and onto the target tissue in a pattern so that any variation in the size of the pattern is minimal as the spacing between the handpiece housing and the target tissue is varied.

15. A method as recited in claim 14 wherein the step of moving the scanning mirror includes independently moving two mirrors to project a two-dimensional pattern of the laser beam on the lens.

16. A method as recited in claim 14 further comprising the step of focusing the laser beam onto the scanning mirror.

17. A method as recited in claim 14 further comprising the step of providing a collimated laser beam to the scanning mirror.

18. A method of ablating a pattern of tissue using a laser beam generated by a laser and delivered to the tissue by a delivery device having a housing comprising the steps of:

positioning an output end of a delivery device housing adjacent the tissue to be ablated;

energizing the laser to generate a laser beam;

directing the laser beam within the delivery device housing through a scanning mirror and a lens to the tissue, wherein the lens has a focal length and the scanning mirror is located at a distance from the lens that is substantially equal to the focal length so that the lens projects the laser beam through an output end of the delivery device housing along a path parallel to an optical axis of the lens; and moving the scanning mirror to project a pattern of laser beams on the tissue.

* * * * *